United States Patent
Saba et al.

(10) Patent No.: US 9,504,522 B2
(45) Date of Patent: Nov. 29, 2016

(54) ELECTROCARDIOGRAM NOISE REDUCTION

(71) Applicant: BIOSENSE WEBSTER (ISRAEL), LTD., Yokneam (IL)

(72) Inventors: Eitan Moshe Saba, Haifa (IL); Yevgeny Bonyak, Haifa (IL); Michael Levin, Haifa (IL); Roy Urman, Karkur (IL); Yoav Lichtenstein, Raanana (IL); Liron Shmuel Mizrahi, Kiryat Bialik (IL); Eyal Yechezkel Glottmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 343 days.

(21) Appl. No.: 13/926,299

(22) Filed: Jun. 25, 2013

(65) Prior Publication Data

US 2014/0378902 A1    Dec. 25, 2014

(51) Int. Cl.
*A61B 18/14*    (2006.01)
*A61B 5/0245*    (2006.01)
(Continued)

(52) U.S. Cl.
CPC ......... *A61B 18/1492* (2013.01); *A61B 5/0245* (2013.01); *A61B 5/0428* (2013.01); *A61B 5/7217* (2013.01); *A61B 5/04023* (2013.01); *A61B 2018/00011* (2013.01); *A61B 2018/00815* (2013.01); *A61B 2018/00821* (2013.01);
(Continued)

(58) Field of Classification Search
CPC .............. A61B 5/0402; A61B 5/0006; A61B 2017/00044; A61B 2018/1472; A61B 5/04026; A61B 5/0428; A61B 5/7217; A61B 5/04023; A61B 2562/0285; A61B 2562/182; A61B 2018/00011; A61B 5/0004; A61M 2230/04; A61M 2210/125; A61N 1/3682
USPC ........... 604/892.1, 118, 34, 36, 73; 600/509, 600/510–528; 361/42
See application file for complete search history.

(56) References Cited

U.S. PATENT DOCUMENTS 3,880,146 A * 4/1975 Everett et al. ................ 600/523
4,519,792 A * 5/1985 Dawe ............................ 604/152
(Continued)

FOREIGN PATENT DOCUMENTS

DE    86 04 749 U1    4/1986
EP    1 169 976 A1    1/2002
(Continued)

OTHER PUBLICATIONS

European Search Report dated Dec. 12, 2014 from corresponding European Patent Application No. 14173982.1.
(Continued)

*Primary Examiner* — Imani Hayman
*Assistant Examiner* — Hamza Darb (57) ABSTRACT

Methods and systems of catheterization include a flexible catheter adapted for insertion into a heart of a living subject. The catheter has a lumen for passing an electrically conductive fluid therethrough with the fluid exiting the catheter at the distal portion. The lumen is connectable to an irrigation pump to form a fluid communication therewith. A fluid reservoir connected to the lumen supplies the fluid to the catheter. Electrocardiogram circuitry is connectable to the subject for monitoring electrical activity in the heart. An electrically conductive cable diverts induced charges in the fluid from the catheter electrodes, for example by connection to an isolated ground of the electrocardiogram.

8 Claims, 9 Drawing Sheets

(51) Int. Cl.
*A61B 5/00* (2006.01)
*A61B 5/0428* (2006.01)
*A61B 5/0402* (2006.01)
*A61B 18/00* (2006.01)

(52) U.S. Cl.
CPC ............... *A61B2018/00839* (2013.01); *A61B 2034/2051* (2016.02); *A61B 2217/007* (2013.01); *A61B 2218/002* (2013.01); *A61B 2505/05* (2013.01); *A61B 2562/182* (2013.01)

(56) References Cited

U.S. PATENT DOCUMENTS

| | | | |
|---|---|---|---|
| 4,644,960 A * | 2/1987 | Johans | 607/122 |
| 5,944,022 A * | 8/1999 | Nardella et al. | 128/899 |
| 6,226,542 B1 * | 5/2001 | Reisfeld | 600/407 |
| 6,301,496 B1 | 10/2001 | Reisfeld | |
| 6,814,733 B2 | 11/2004 | Schwartz | |
| 6,892,091 B1 | 5/2005 | Ben-Haim | |
| 6,997,924 B2 | 2/2006 | Schwartz | |
| 7,156,816 B2 | 1/2007 | Schwartz | |
| 7,536,218 B2 | 5/2009 | Govari | |
| 7,756,576 B2 | 7/2010 | Levin | |
| 7,785,284 B2 | 8/2010 | Baraldi | |
| 8,311,628 B2 | 11/2012 | Stevenson | |
| 2009/0198300 A1* | 8/2009 | Zhang et al. | 607/28 |
| 2012/0046562 A1 | 2/2012 | Powers et al. | |
| 2012/0165735 A1 | 6/2012 | Keh | |
| 2012/0282126 A1 | 11/2012 | Brandt et al. | |

FOREIGN PATENT DOCUMENTS

| | | |
|---|---|---|
| EP | 2 604 211 A1 | 6/2013 |
| FR | 2 909 003 A1 | 5/2008 |
| WO | WO 2004/108206 A1 | 12/2004 |
| WO | WO 2009/044220 A1 | 4/2009 |
| WO | WO 2012/173697 A1 | 12/2012 |

OTHER PUBLICATIONS

Santosh I. Patel, et al., "Equipment-related Electrocardiographic Artifacts", Anesthesiology, Jan. 1, 2008, pp. 138-148, vol. 108, No. 1.

* cited by examiner

| SETUP | BI POLAR NOISE | |
|---|---|---|
| | CDF 95 | MAX |
| NOMINAL | 207 | 255 |
| 10K TO GROUND | 114 | 156 |
| TWO WIRES | 120 | 192 |
| ONE WIRE | 120 | 129 |

| SETUP | UNI POLAR NOISE | | | | | | | | | |
|---|---|---|---|---|---|---|---|---|---|---|
| | MEAN | | | | | MAX | | | | |
| NOMINAL | 222.0 | 25.3 | 24.5 | 24.2 | 28.6 | 28.7 | 393.0 | 33.0 | 33.0 | 33.0 | 39.0 | 42.0 |
| 10K TO GROUND | 219.2 | 30.2 | 31.0 | 30.4 | 35.0 | 35.9 | 342.0 | 42.0 | 45.0 | 42.0 | 48.0 | 51.0 |
| TWO WIRES | 180.8 | 25.7 | 26.8 | 26.2 | 31.8 | 32.3 | 180.8 | 25.7 | 26.8 | 26.2 | 31.8 | 32.3 |
| ONE WIRE | 194.2 | 27.2 | 28.1 | 27.7 | 33.3 | 33.7 | 270.0 | 36.0 | 39.0 | 36.0 | 48.0 | 48.0 |

ELECTROCARDIOGRAM NOISE REDUCTION

BACKGROUND OF THE INVENTION

Field of the Invention

This invention relates to medical catheterization. More particularly, this invention relates to electrocardiographic monitoring during medical catheterization procedures.

Description of the Related Art

The meanings of certain acronyms and abbreviations used herein are given in Table 1.

TABLE 1

Acronyms and Abbreviations

| | |
|---|---|
| ECG | Electrocardiogram |
| PIU | Patient Interface Unit |
| RF | Radiofrequency |

Medical catheterizations are routinely carried out today. For example, in cases of cardiac arrhythmias, such as atrial fibrillation, which occur when regions of cardiac tissue abnormally conduct electric signals to adjacent tissue, thereby disrupting the normal cardiac cycle and causing asynchronous rhythm. Procedures for treating arrhythmia include surgically disrupting the origin of the signals causing the arrhythmia, as well as disrupting the conducting pathway for such signals. By selectively ablating cardiac tissue by application of energy, e.g., radiofrequency energy via a catheter, it is sometimes possible to cease or modify the propagation of unwanted electrical signals from one portion of the heart to another. The ablation process destroys the unwanted electrical pathways by formation of non-conducting lesions.

A known difficulty in the use of radiofrequency energy for cardiac tissue ablation is controlling local heating of tissue. There are tradeoffs between the desire to create a sufficiently large lesion to effectively ablate an abnormal tissue focus, or block an aberrant conduction pattern, and the undesirable effects of excessive local heating. If the radiofrequency device creates too small a lesion, then the medical procedure could be less effective, or could require too much time. On the other hand, if tissues are heated excessively then there could be local charring effects due to overheating. Such overheated areas can develop high impedance, and may form a functional barrier to the passage of heat. The use of slower heating provides better control of the ablation, but unduly prolongs the procedure.

Commonly assigned application Ser. No. 13/339,782, which is herein incorporated by reference, discloses the use of an irrigation pump to cause irrigation fluid to flow through a lumen of the catheter in order to cool the ablation site.

SUMMARY OF THE INVENTION

There is provided according to embodiments of the invention a catheterization system, which avoids spurious electrical interference in electrical monitoring circuitry when a peristaltic pump is operating to irrigate an ablation site. The system includes a flexible catheter adapted for insertion into a heart of a living subject, the catheter having a lumen for passing an electrolyte-containing fluid therethrough to exit the catheter at its distal portion. A fluid reservoir is connected to the irrigation pump for supplying the electrolyte-containing fluid to the catheter lumen. Electrocardiogram circuitry is connectable to the subject for monitoring electrical activity in the heart. A conductive cable electrically connects the electrolyte-containing fluid with the input of the electrocardiogram circuitry.

According to a further aspect of the system, the electrically conductive cable leads from the fluid reservoir to an isolated ground through a resistor, and the electrocardiogram circuitry is connected to the isolated ground.

According to yet another aspect of the system, the resistor has a resistance of between $0\Omega$ and $10\ K\Omega$.

According to still another aspect of the system, the resistor has a resistance of between $0\Omega$ and $3\ M\Omega$.

According to another aspect of the system, a drip chamber is connected to the fluid reservoir for receiving the electrolyte-containing fluid therein, and the electrically conductive cable is connected to the electrolyte-containing fluid downstream of the drip chamber.

According to yet another aspect of the system the irrigation pump has an inlet hydraulic line and an output hydraulic line, and an electrically conductive link between the electrolyte-containing fluid in the inlet hydraulic line and the electrolyte-containing fluid in the output hydraulic line. The electrically conductive link may be connected to an isolated ground of the electrocardiogram circuitry.

There is further provided according to embodiments of the invention a catheterization system, including a flexible catheter adapted for insertion into a heart of a living subject. The catheter has a lumen for passing an electrically conductive fluid therethrough to exit the catheter at its distal portion. The lumen is connectable to an irrigation pump to form a fluid communication therewith. A fluid reservoir supplies the electrically conductive fluid to lumen the catheter with the aid of the irrigation pump. Electrocardiogram circuitry is connectable to the subject for monitoring electrical activity in the heart. An electrical shield is disposed about the fluid reservoir and connected to the input of the electrocardiogram circuitry.

According to one aspect of the system, the electrocardiogram circuitry is connected to the subject via a metallically shielded electrical conductor leading through the catheter to an electrode at the distal portion thereof, and the shielded electrical conductor is incorporated in the hydraulic line.

There is further provided according to embodiments of the invention a catheterization system, including a flexible catheter adapted for insertion into a heart of a living subject, the catheter having and a lumen for passing an electrically conductive fluid therethrough to exit the catheter at its distal portion. The lumen is connectable to an irrigation pump to form a fluid communication therewith. A fluid reservoir is connected to the irrigation pump for supplying the electrically conductive fluid to the catheter. Electrocardiogram circuitry is connectable to the subject for monitoring electrical activity in the heart, and an electrically conductive cable links the electrically conductive fluid of the fluid reservoir to a body surface electrode on the subject.

There is further provided according to embodiments of the invention a method of catheterization, which is carried out by Inserting a flexible catheter into a heart of a living subject, pumping an electrolyte-containing fluid from a fluid reservoir through a lumen of the catheter using a peristaltic pump, connecting electrocardiogram circuitry to the subject for monitoring electrical activity in the heart, connecting an electrically conductive cable between the electrolyte-containing fluid of the fluid reservoir and the input of the electrocardiogram circuitry, and while pumping the electrolyte-containing fluid processing electrical data from the subject in the electrocardiogram circuitry.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

Aspects of the present invention may be embodied in software programming code, which is typically maintained in permanent storage, such as a computer readable medium. In a client/server environment, such software programming code may be stored on a client or a server. The software programming code may be embodied on any of a variety of known nontransitory media for use with a data processing system, such as USB memory, hard drive, electronic media or CD-ROM. The code may be distributed on such media, or may be distributed to users from the memory or storage of one computer system over a network of some type to storage devices on other computer systems for use by users of such other systems.

Definitions

"Noise" is a disturbance, including a random and persistent disturbance that obscures or reduces the clarity of a signal.

A "patient interface unit" (PIU) provides an interface between analog input signals and a digital data processing system.

System Description

Figure 1:
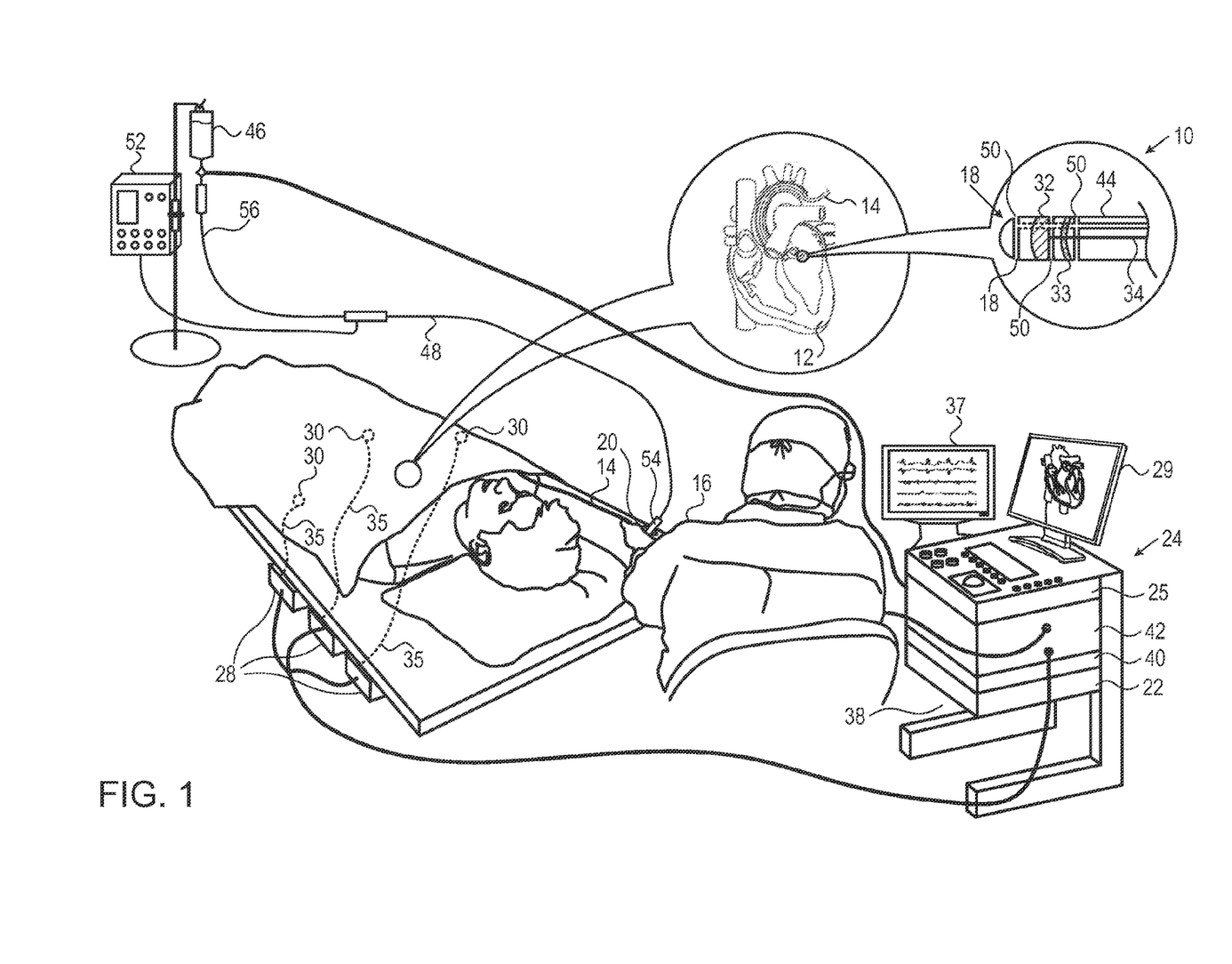
FIG. 1 is a pictorial illustration of a system for performing catheterization procedures on a heart of a living subject, which is constructed and operative in accordance with an embodiment of the invention.

Turning now to the drawings, reference is initially made to FIG. 1, which is a pictorial illustration of a system 10 for performing exemplary catheterization procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall at an ablation target site. Electrical activation maps, anatomic positional information, i.e., of the distal portion of the catheter, and other functional images may then be prepared using a processor 22 located in a console 24, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765, which is capable of producing electroanatomic maps of the heart as required. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current from a radiofrequency (RF) generator 40 through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a positioning processor 22, located in the console 24.

Ablation energy and electrical signals can be conveyed to and from the heart 12 through the catheter tip and an ablation electrode 32 located at or near the distal tip 18 via cable 34 to the console 24. Pacing signals and other control signals may be also conveyed from the console 24 through the cable 34 and the ablation electrode 32 to the heart 12. Sensing electrodes 33, also connected to the console 24 are disposed between the ablation electrode 32 and the cable 34.

Wire connections 35 link the console 24 with body surface electrodes 30 and other components of a positioning sub-system. The electrode 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near each of the electrode 32.

The console 24 typically contains one or more ablation power generators 25. The catheter 14 may be adapted to conduct ablative energy to the heart using radiofrequency energy. Such methods are disclosed in commonly assigned U.S. Pat. Nos. 6,814,733, 6,997,924, and 7,156,816, which are herein incorporated by reference.

The positioning processor 22 is an element of a positioning subsystem in the system 10 that measures location and orientation coordinates of the catheter 14.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem may employ impedance measurement, as taught, for example, in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. The processor 22 is typically a computer with appropriate signal processing circuits. The processor 22 is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received via cable 38 and used by the console 24 and the positioning system to compute the position and orientation of the catheter 14 and analyze the electrical signals from the electrodes, and generate desired electroanatomic maps.

The system 10 may include an electrocardiogram (ECG) monitor 37, coupled to receive signals from one or more body surface electrodes. The ECG signal is typically received through an interface with the console 24, e.g., a patient interface unit 42 having an analog input and an isolated ground may be used to provide an ECG synchronization signal to the console 24. The patient is normally grounded to the isolated ground.

An electrically conductive fluid, e.g., saline, Ringer's lactate, is delivered through a lumen 44 in the catheter 14 from a reservoir 46 via a hydraulic line 48. The electrically conductive fluid is generally referred to herein as "saline" for convenience, it being understood that this is by way of example and not of limitation. The lumen 44 terminates in exit pores 50 through which the liquids emerge to cool the electrode 32 and the ablation site. A pump 52 is connected to the hydraulic line 48 and causes the fluid to be delivered to the catheter 14 through an entrance port 54 at a desired rate. One difficulty with such an arrangement is that operation of equipment in the environment, e.g., the pump 52, produces electrical emissions, which produce noise that can be picked up by the hydraulic line 48 and interfere with the analysis and display of the ECG on the monitor 37.

First Embodiment

The inventors have found that connecting an electrically conductive wire 56 between the electrolytic fluid, e.g., between the reservoir 46, and the isolated ground of the analog front end of the interface unit 42 effects a significant reduction in the electrical interference.

In order to minimize the number of conductors in the area of operation, the wire 56 may be incorporated in the hydraulic line 48 leading from the reservoir 46.

Figure 2:
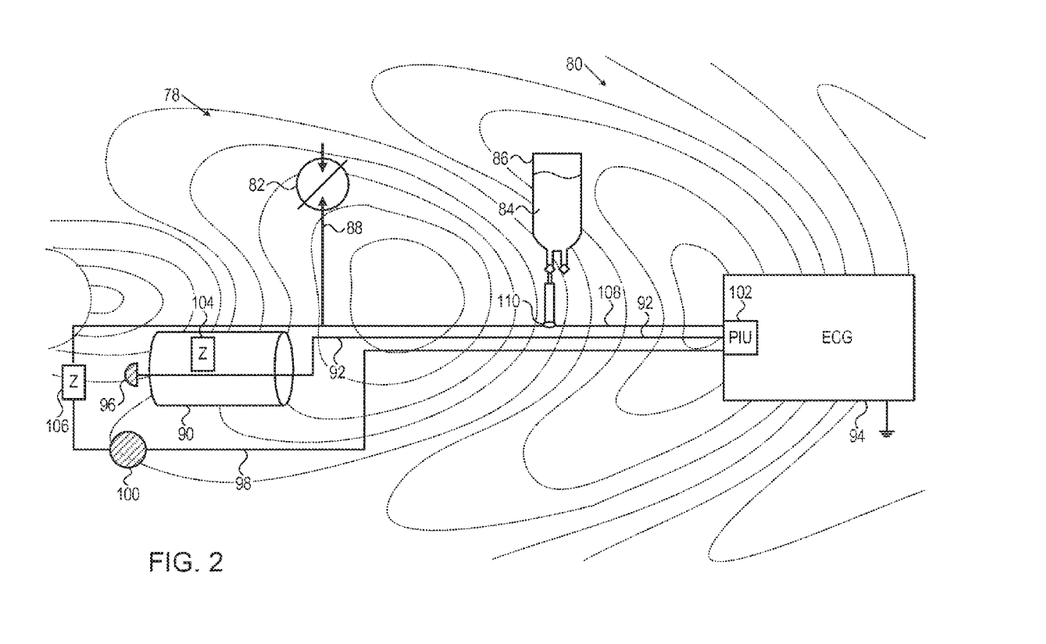
FIG. 2 is a schematic diagram of a system for reducing electrocardiogram noise, in accordance with an embodiment of the invention.

Reference is now made to FIG. 2, which is a schematic diagram of a system 78 for reducing electrocardiogram noise, in accordance with an embodiment of the invention. The system operates in an environment in which an electromagnetic field 80 exists, and which may be produced in part by a hydraulic pump 82, which propels an electrolytic fluid, e.g., a saline solution 84 from a reservoir 86, such as an intravenous bottle or bag. The saline solution 84 flows through line 88, and through a catheter 90. An electrical conductor 92 extends from the distal portion of the catheter 90 to ECG circuitry 94.

The electrical conductivity of the saline solution 84 is sufficient for it to function as an effective antenna. As the catheter 90 may be several meters in length, the saline solution 84 in the catheter 90 can pick up and radiate the electromagnetic emissions 80, which is then perceived as noise on the cardiac electrogram measured from the catheter's tip electrode 96 and on an electrocardiogram employing standard leads 98.

Capacitive coupling may occur between the line 88 and ECG leads 98 and ECG pads 100 and between the line 88 and the conductor 92 within the catheter 90 that may connect to a programmable interface unit (PIU) input 102. Such coupling, represented by mutual impedances (Z) 104, 106, may account in part for communication of electrical noise originating in the pump 82 or RF generator 40 (FIG. 1) or elsewhere in the environment to the ECG circuitry 94. In general the impedances 104, 106 do not have the same magnitude or phase angle.

A short circuit connects the electrolyte to the ECG circuitry 94, e.g., via the PIU input 102, using a low impedance wire 108. The connection to the reservoir 86 should be made using a connector 110 disposed downstream of a drip chamber 112. When the wire 108 is connected as shown in FIG. 2, substantial reduction in noise is experienced when the pump 82 or other equipment relating to the catheterization procedure, e.g., the RF generator 40 (FIG. 1) is in operation.

Example

Figure 3:
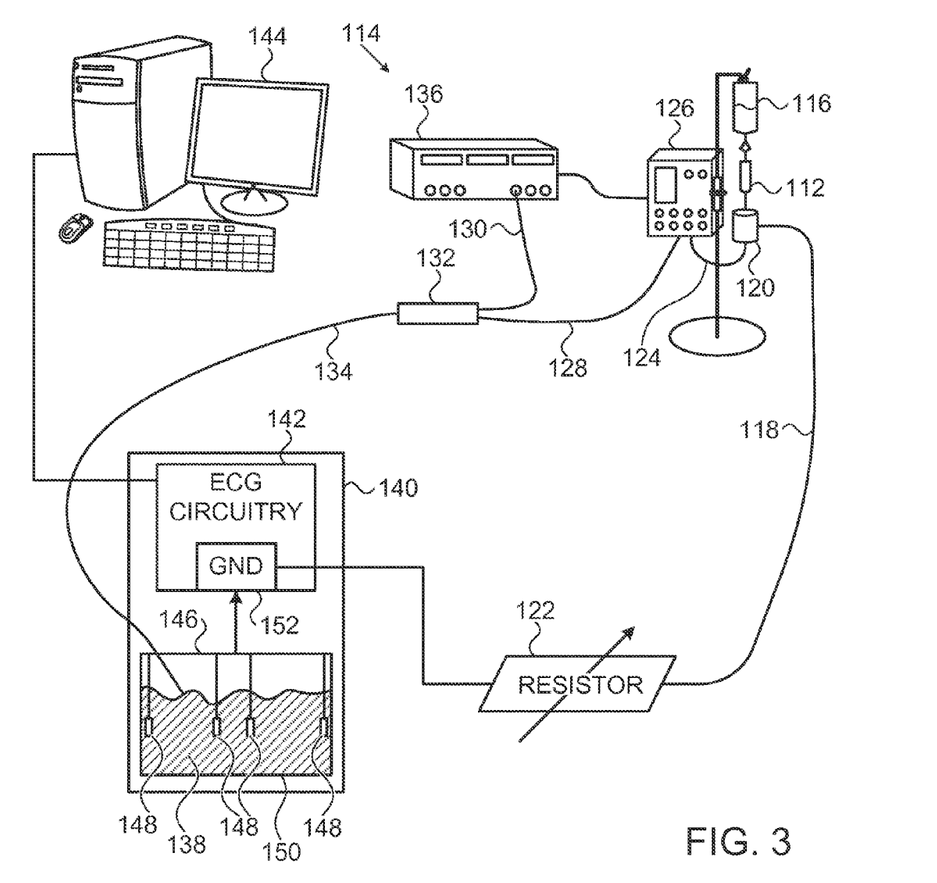
FIG. 3 is a schematic diagram of a test arrangement for measuring electrocardiogram noise reduction, in accordance with an embodiment of the invention.

Reference is now made to FIG. 3, which is a schematic diagram of a test arrangement 114 using an RF signal generator, in accordance with an embodiment of the invention. An intravenous infusion pack 116, containing saline, constitutes an electrolyte fluid reservoir, as described above. A cable 118, leading from the intravenous infusion pack 116, is connected to an isolated ground by a conductive cable 118 that extends from a metal connector 120 through an adjustable resistor 122. The saline flows from the drip chamber 112 through the connector 120 to reach a line 124, and is in electrical contact with the cable 118. The line 124 extends from the connector 120 to a pump 126.

Measurements of electrical noise were conducted using values of 0Ω and 10 KΩ for the resistor 122. In practice values of up to 5 MΩ are usable to avoid signal distortion that would result from a direct liquid connection to ground. For testing purposes values of 0-10 KΩ were chosen. Hydraulic lines 124, 128 interconnect the intravenous infusion pack 116, and the pump 126. An electrical Line 130 connects a handle 132 and a catheter 134 with an RF generator 136. The line 128 extends from the pump 126 to the handle 132 of catheter 134. The distal end of the catheter 134 is inserted into an aquarium 150 containing saline 138, which emulates a human subject. The cable 118 and resistor 122 may be embedded into the wall of hydraulic lines or may be external to the hydraulic lines.

A test subsystem 140 includes ECG circuitry 142, which is connected to a display 144. Four ECG leads 146 are connected to the ECG circuitry 142 and to metal patches 148 that are mounted on the internal surfaces of an aquarium 150 in contact with the saline 138. The cable 118 connects the intravenous infusion pack 116 to an isolated ground 152 in the ECG circuitry 142 via resistor 122 that can have a value of 0-10 KΩ.

Figure 4:
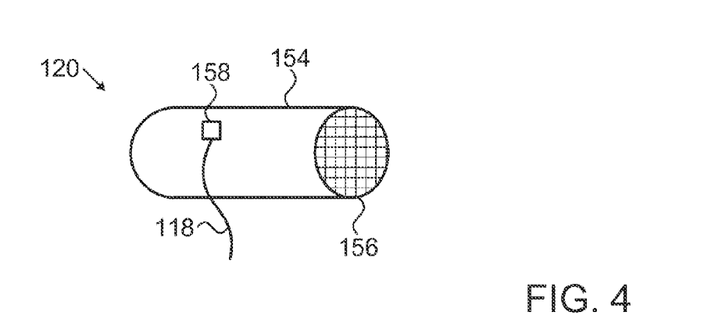
FIG. 4 is a schematic diagram of a connector for establishing electrical continuity between fluid and an electrical cable, which is constructed in accordance with an embodiment of the invention.

Reference is now made to FIG. 4, which is a schematic diagram of the connector 120 (FIG. 3), which is constructed in accordance with an embodiment of the invention. The connector 120 is tubular, having an outer metal shell 154, and a lumen filled with an electrically conductive net or sponge 156. The sponge 156 assures extensive physical contact with saline flowing in the lumen of the connector 120, and increases its conductance. An electrical connector 158 is provided on the metal shell 154 so that electrical continuity exists between the saline in the lumen, the sponge 156 and the cable 118.

A suitable test protocol for evaluating the embodiments described herein follows:

Test Setup.

Connect the Catheter to the PIU magnetic navigation catheter (MAP) input. Fill the aquarium with saline. Connect all four ECG limb channels (right leg, right arm, left arm and left leg) to different sides of the interior wall of aquarium using previously installed metal patches, which are in contact with the saline 138. Connect the RF generator to the PIU. Connect the irrigation pump to the catheter, and set the flow rate to 30 ml/min.

Test Procedure.

Set up a MATLAB® Application adapter DLL (Mex-DLL) to acquire ECG data from electrodes M1-M6.

Open relevant ECG channels. Set sampling rate to 1 KHz. Acquire 1200 packets (20 packets per second, 60 seconds test) of ECG data.

Calculate bipolar noise between the next couples: M2-M1.

Data Analysis

Every 400 ms, calculate the following cumulative distribution function (CDF95):

MAX(BiPolarNoise[uV])=Max($M2-M1$)-MIN($M2-M1$); and

CDF95(BiPolarNoise[uV])=CDF95$_t$($M2-M1$).

Figure 5:
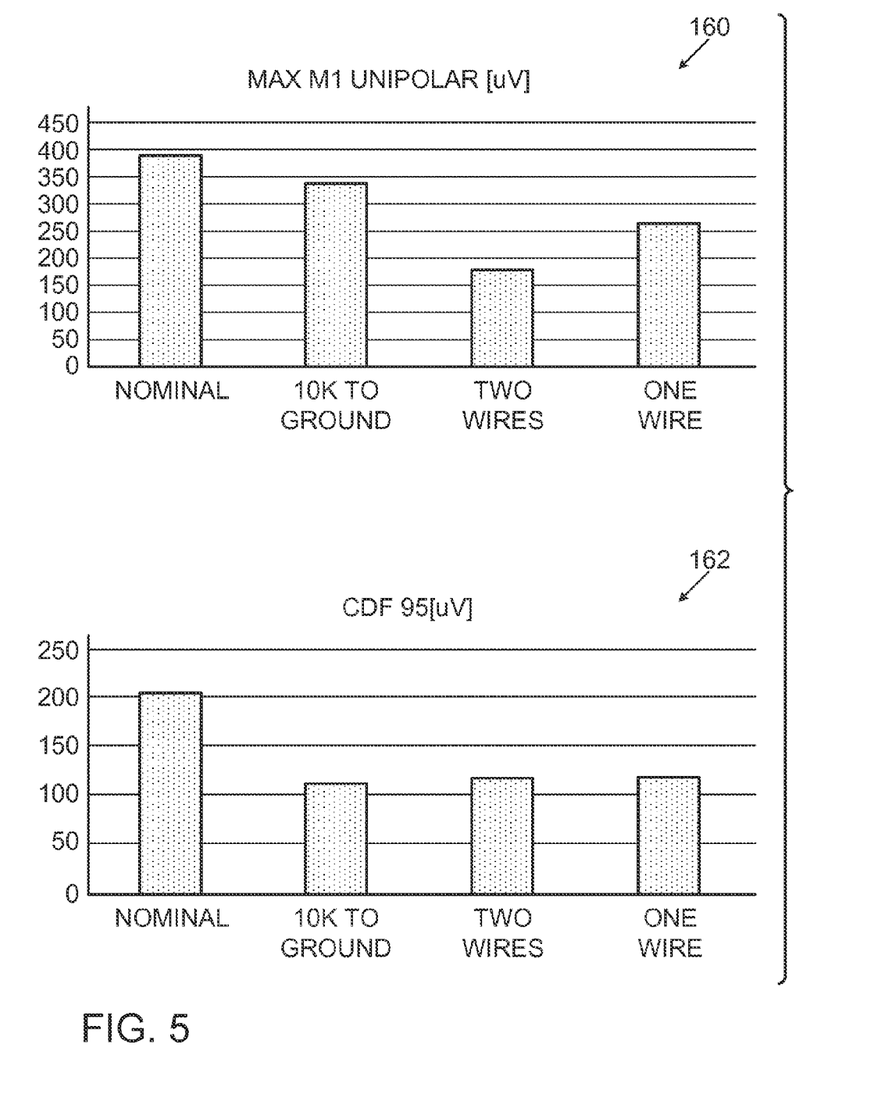
FIG. 5 shows two bar charts indicating performance of the test arrangement shown in FIG. 3.

Reference is now made to FIG. 5, which is a collection of two bar charts indicating performance of the test arrangement 114 (FIG. 3), in accordance with an embodiment of the invention. Charts 160, 162 indicate noise levels when the leads 146 are set up in unipolar and bipolar configurations, respectively. All configurations show improvement, when compared to the nominal values at the left of the charts. Nominal values were obtained using a conventional arrangement in which the cable 118 was not connected. The CDF95 values shown on the vertical axis of chart 162 reflect the noise level that includes 95% of the observed noise.

Figure 6:
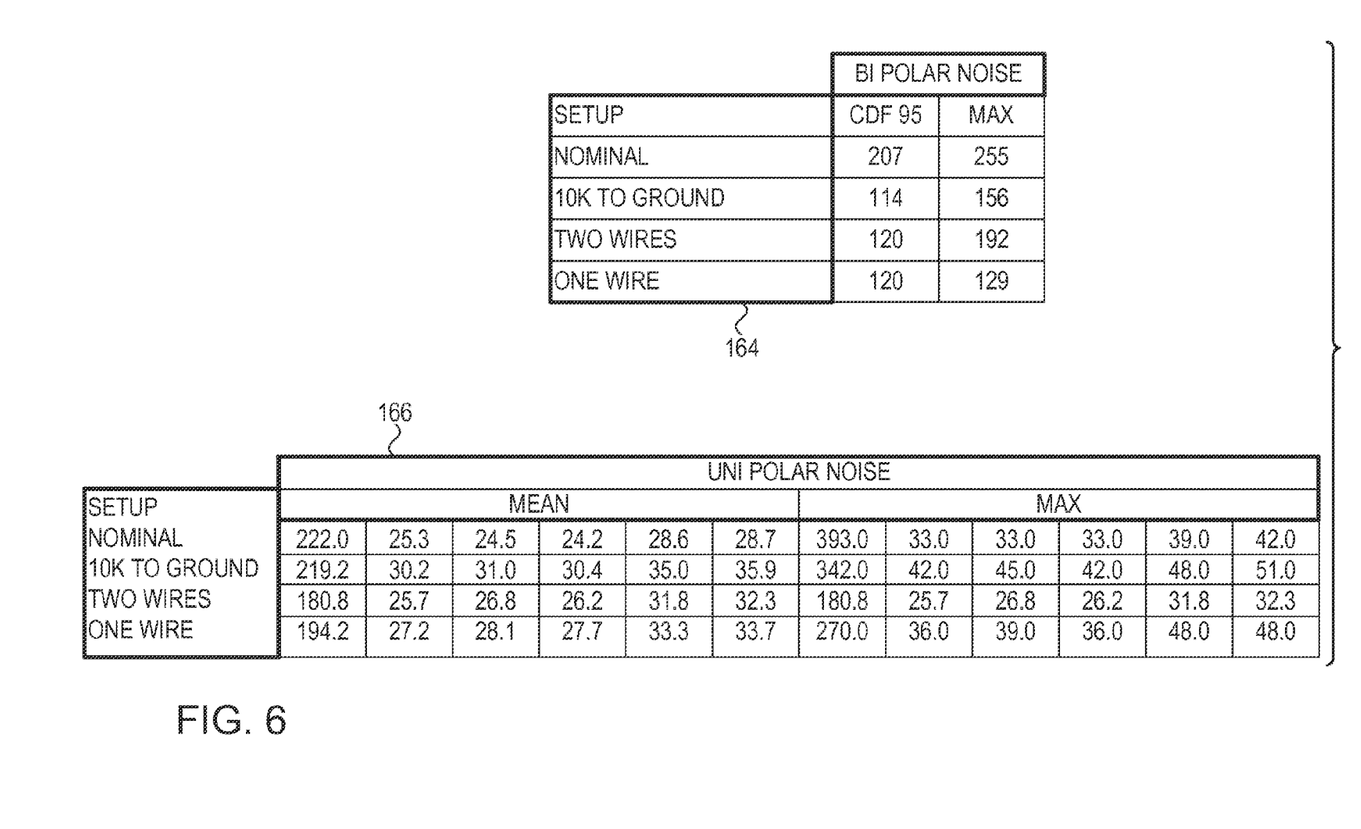
FIG. 6 shows two tables showing the performance of versions of the test arrangement shown in FIG. 3.

Reference is now made to FIG. 6, which shows two tables 164, 166, showing the performance of versions of the test arrangement 114 (FIG. 3) with respect to noise reduction in bipolar and unipolar configurations, respectively.

Second Embodiment

Figure 7:
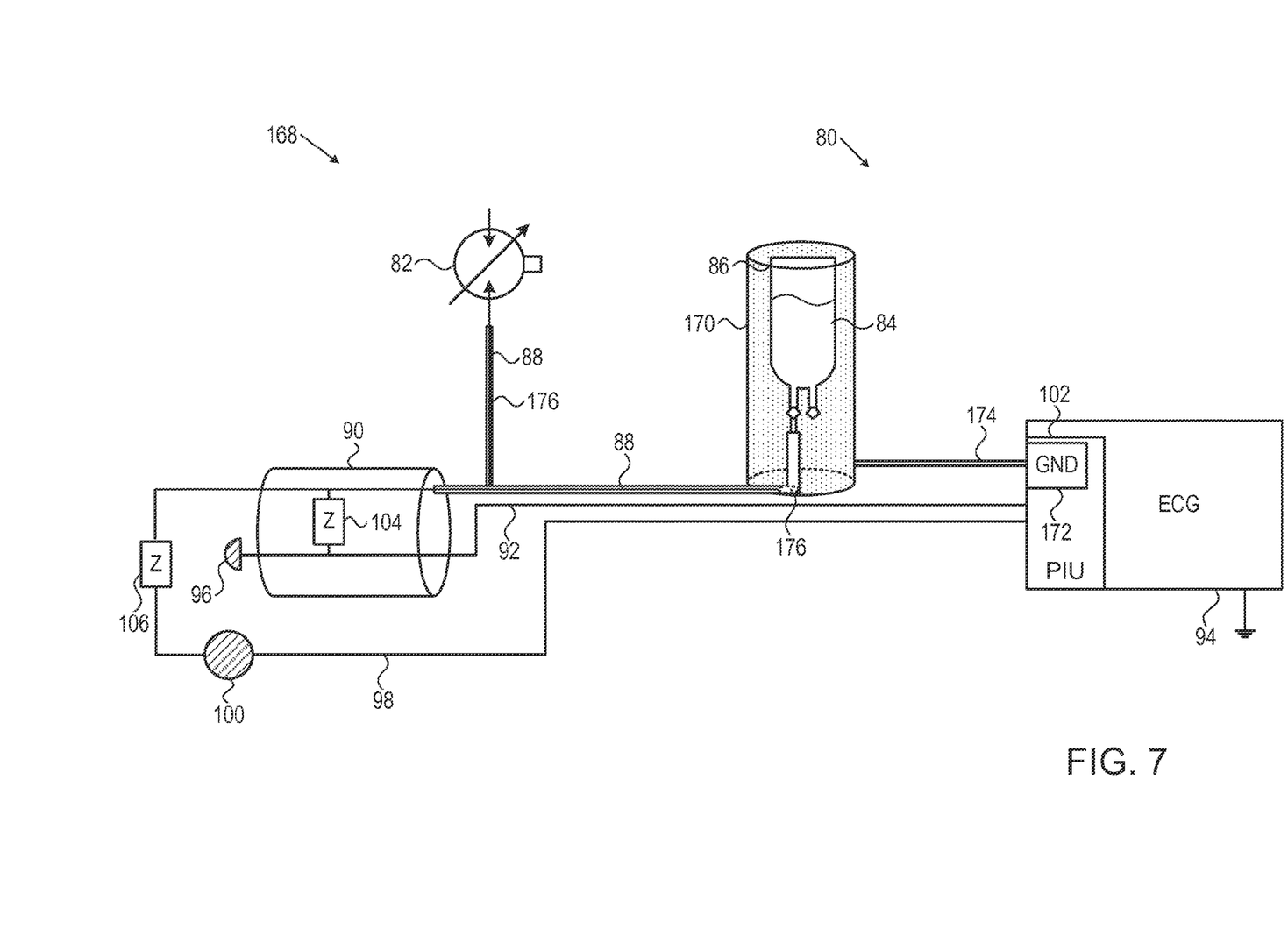
FIG. 7 is a schematic diagram of a system for reducing electrocardiogram noise, in accordance with an alternate embodiment of the invention.

Reference is now made to FIG. 7, which is a schematic of a system 168 for reducing electrocardiogram noise, in accordance with an alternate embodiment of the invention. A metal shield 170 surrounds the reservoir 86 and is connected to an isolated ground 172 in the PIU input 102 by a shielded cable 174. With the shield 170 in place during operation, noise picked up by the ECG circuitry 94 is effectively reduced.

Additionally or alternatively the line 88 may be electrically shielded, for example by including the line 88 in a metallically shielded cable 176, which extends from the pump 82 and the reservoir 86 to the catheter 90. The shielded cable can be, for example coaxial cable. The leads 98 may also be shielded.

Further additionally or alternatively, the reservoir 86 may be connected to an isolated ground as described above.

Third Embodiment

Figure 8:
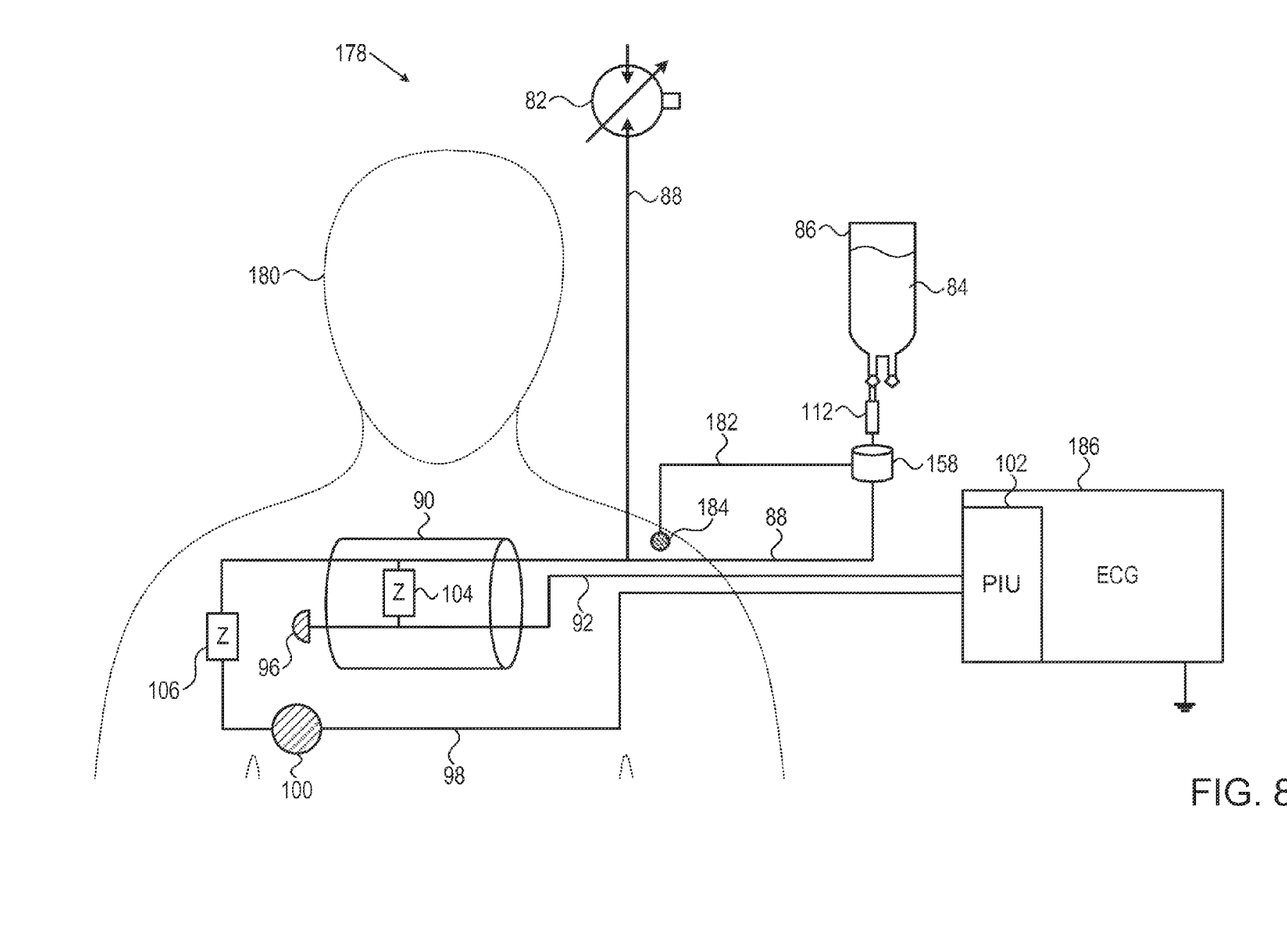
FIG. 8 is a schematic diagram of a system for reducing electrocardiogram noise, in accordance with an alternate embodiment of the invention.

Reference is now made to FIG. 8, which is a schematic of a system 178 for reducing electrocardiogram noise, in accordance with an alternate embodiment of the invention. In this embodiment the reservoir 86 is connected to a subject 180 by an electrically conductive cable 182, for example using a body surface electrode pad 184 attached to a limb or other portion of the body. The cable 182 may be shielded as described above. The connector 158 is placed in hydraulic line 88 downstream from the drip chamber 112, as described above in the discussion of FIG. 3. The electrode 96 is connected by conductor 92 to a console 186 containing ECG circuitry and an RF ablation generator. The features of this embodiment may be combined with any of the other embodiments described above.

Fourth Embodiment

Figure 9:
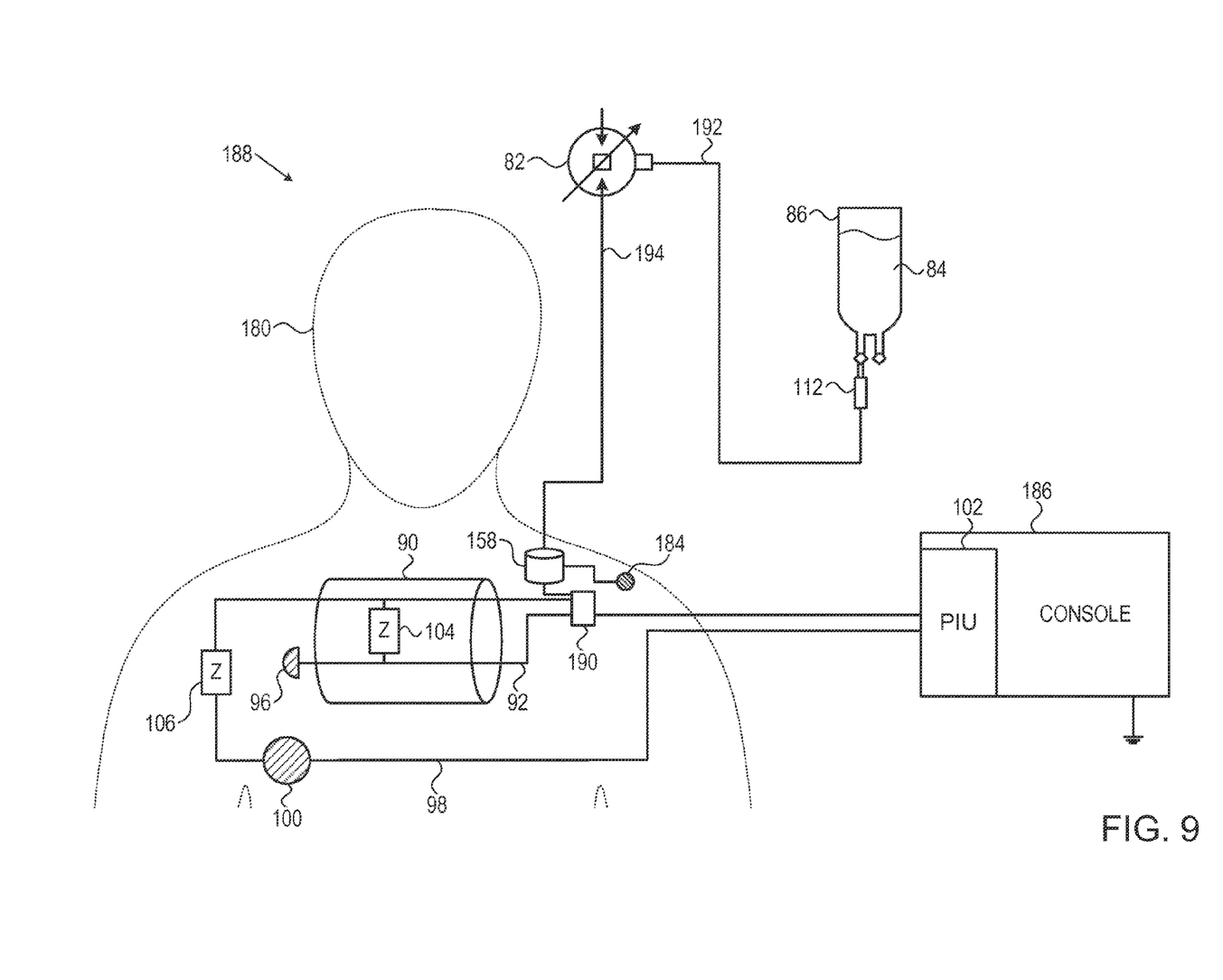
FIG. 9 is a schematic diagram of reducing electrocardiogram noise, in accordance with an alternate embodiment of the invention.

Reference is now made to FIG. 9, which is a schematic of a system 188 for reducing electrocardiogram noise, in accordance with an alternate embodiment of the invention. The arrangement in FIG. 9 is similar that of FIG. 8. However, the reservoir 86, the pump 82 and a catheter handle 190 are now connected in series. The reservoir 86 and the inflow of the pump 82 are directly connected via a hydraulic line 192. The outflow of the pump 82 is conducted to the connector 158 by a hydraulic line 194. The connector 158 is located downstream of the pump 82 near the catheter handle 190. The connector 158 is shorted to the electrode pad 184 on the subject 180 via the cable 182.

It is desirable to locate the electrode pad 184 as far as possible from the electrode 96. Thus the electrode pad 184 could be placed on the distal portion of a lower extremity.

In some embodiments a plurality of connectors may be placed along the line 194 between the pump 82 and the handle 190. Electrical interference that is believed to be produced by an interaction between pump 82 and the saline in the hydraulic lines is reduced as long as the electrical resistance of the path through connectors 158, the electrode pad 184 and the subject 180 is less than the resistance of the path through the subject 180 via the saline in the hydraulic lines and the saline-irrigated electrode 96.

Fifth Embodiment

Figure 10:
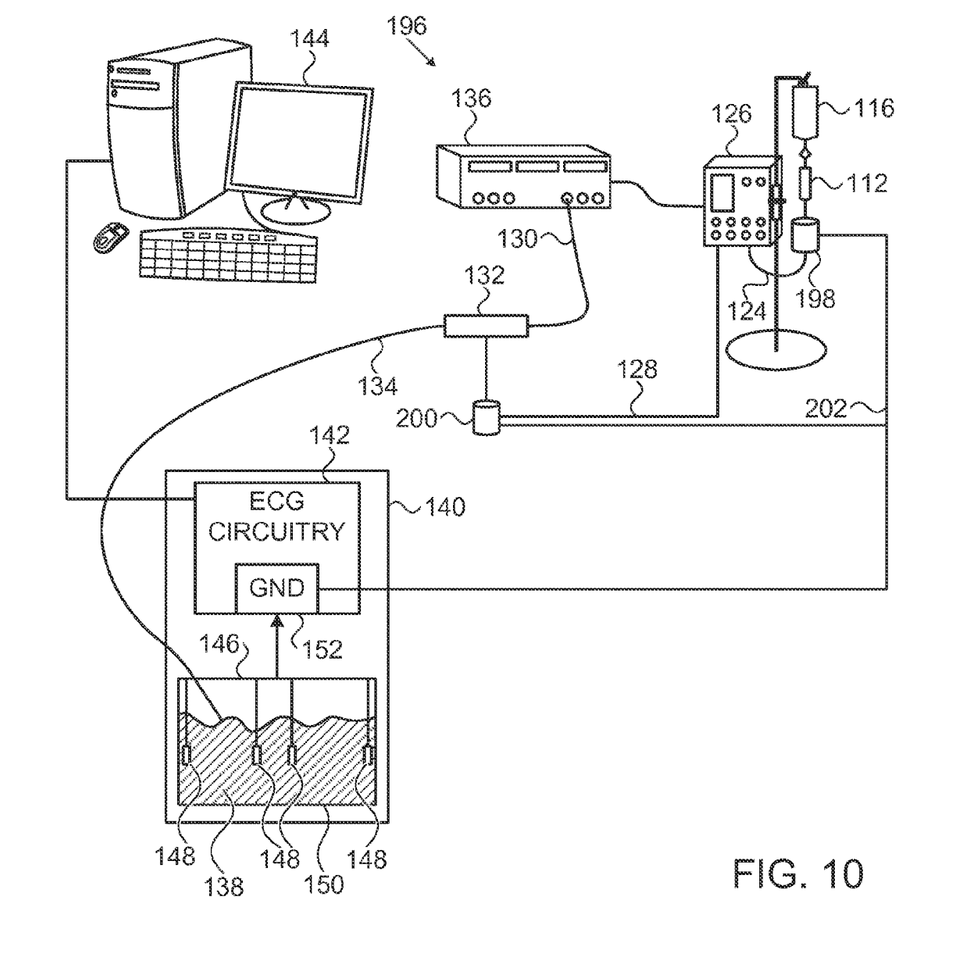
FIG. 10 is a schematic diagram of a test arrangement of an infusion system in accordance with an alternate embodiment of the invention.

Reference is now made to FIG. 10, which is a schematic diagram of a test arrangement 196 of an infusion system using an RF signal generator, in accordance with an alternate embodiment of the invention. This embodiment is particularly effective in eliminating pump-induced noise that does not primarily result from an antenna effect, but is believed to have other causes, possibly a piezoelectric effect caused by moving parts of the pump and the tubing.

Figure 11:
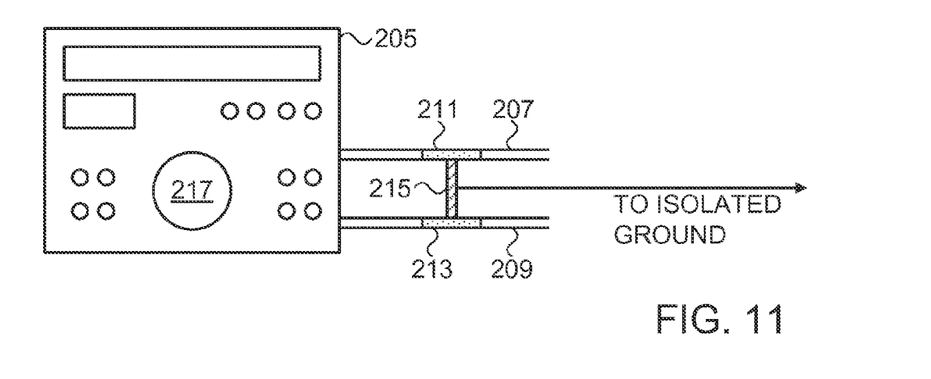
FIG. 11 is a schematic diagram of a pump which has been modified for noise reduction, in accordance with an embodiment of the invention.

Two conductive connectors 198, 200 are inserted in the fluid stream upstream and downstream of the pump 126 in the lines 124, 128, respectively. The connectors 198, 200, which may have the same construction as the connector 120 (FIG. 5), are shorted together by an electrically conductive wire 202. The connectors 198, 200 may be positioned conveniently as shown in FIG. 11. Alternatively, the connectors 198, 200 may be placed immediately before and after the interface to the pump 126. In any case the wire 202 may also connect to the isolated ground of the ECG circuitry 142.

In some embodiments, the electrical connections of the test arrangement 196 and test arrangement 114 (FIG. 4) may be combined. In operation the metal patches 148 and the aquarium 150 are replaced by ECG leads applied to a subject.

Sixth Embodiment

Reference is now made to FIG. 11, which is a schematic diagram of a peristaltic pump 205, which has been modified for noise reduction, in accordance with an embodiment of the invention. The pump 205 has a metallic roller 217 an input line 207 and an output line 209 to which are attached connectors 211, 213, respectively, which may have the same construction as the connector 120 (FIG. 4). A link 215 shorts the connectors 211, 213 and may connect to the isolated ground of the EKG circuitry as described above.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A catheterization system, comprising:
a flexible catheter adapted for insertion into a heart of a living subject, having a distal portion and a lumen for passing an electrolyte-containing fluid therethrough to exit the catheter at the distal portion, the lumen connectable to an irrigation pump to form a fluid communication therewith;
a fluid reservoir connected to the irrigation pump for supplying the electrolyte-containing fluid to the catheter;
electrocardiogram circuitry connectable to the subject for monitoring electrical activity in the heart, the electrocardiogram circuitry having an input; and
an electrically conductive cable linking the electrolyte-containing fluid with the input of the electrocardiogram circuitry through an isolated ground.

2. The system according to claim 1, wherein the electrically conductive cable leads from the fluid reservoir to the isolated ground through a resistor, and the electrocardiogram circuitry is connected to the isolated ground.

3. The system according to claim 2, wherein the resistor has a resistance of between 0Ω and 10KΩ.

4. The system according to claim 2, wherein the resistor has a resistance of between 0Ω and 3 MΩ.

5. The system according to claim 1, further comprising a drip chamber connected to the fluid reservoir for receiving the electrolyte-containing fluid therein, wherein the electrically conductive cable is connected to the electrolyte-containing fluid downstream of the drip chamber.

6. The system according to claim 5, wherein a first segment of a hydraulic line leads from the drip chamber to an input of the irrigation pump, and a second segment leads from an output of the irrigation pump to the catheter, and wherein the electrically conductive cable is further connected to the first segment and to the second segment.

7. The system according to claim 1, wherein the irrigation pump has an inlet hydraulic line and an output hydraulic line, and further comprising an electrically conductive link between the electrolyte-containing fluid in the inlet hydraulic line and the electrolyte-containing fluid in the output hydraulic line.

8. The system according to claim 7, wherein the electrically conductive link is connected to an isolated ground of the electrocardiogram circuitry.

* * * * *